United States Patent [19]

Slater

[11] 4,040,904

[45] Aug. 9, 1977

[54] NOVEL RABIES VIRUS VACCINE AND PROCESSES

[76] Inventor: Eban A. Slater, 1 Lindenwood Lane, St. Joseph, Mo. 64505

[21] Appl. No.: 597,654

[22] Filed: July 21, 1975

[51] Int. Cl.² .................. C12K 7/00; A61K 39/28
[52] U.S. Cl. ........................... 195/1.3; 424/89
[58] Field of Search .................. 195/1.1–1.7; 424/89

[56] References Cited

U.S. PATENT DOCUMENTS 3,423,505  1/1969  Crawley et al. ............... 195/1.3

Primary Examiner—Sam Rosen

[57] ABSTRACT

There is presented herein a novel rabies virus vaccine which has been developed from a known strain and a process for the preparation of the vaccine. One outstanding advantage of the novel strain is the direct correlation of its cytopathic effect on tissue culture cell monolayers and its titre.

5 Claims, No Drawings

NOVEL RABIES VIRUS VACCINE AND PROCESSES

BACKGROUND OF THE INVENTION

Vaccines from several strains of rabies virus have been embployed widely in the immunization of animals.

One strain employed has been the well-known Flury strain which has been used for the immunization of dogs. The Flury strain was isolated by passage of a street virus through chick brains, and was adapted to growth in embryonated eggs.

Vaccines containing the Flury strain of rabies virus have been useful in the immunization of dogs against rabies. However, the Flury vaccine has certain disadvantages. It contains a relatively high amount of undesirable proteins to which the animal being treated may be sensitive and contains a relatively low amount of the active virus.

The E.R.A. strain of rabies virus, was derived from S.A.D. virus, a fixed virus strain, originally isolated from a rabid dog and propagated in mouse brain and hamster kidney cells, and then adapted to primary pig kidney tissue culture. A sample of the ERA strain of rabies virus was deposited with the American Type Culture Collection, Washington, D.C. on Oct. 29, 1964 and was recorded there as number VR 332.

Vaccines containing the ERA strain adapted to primary pig kidney tissue culture are widely used in immunizing various animal species including dogs, cats and cattle against rabies.

In order to determine whether the rabies virus is able to produce a sufficient number of rabies antibodies when injected as a vaccine in animals the serum titer of vaccinated animals is determined. In order to determine such titer a lengthy and tedious process has been employed in which serum-virus neutralization tests are carried out by preparing serial dilutions of serum, mixing with a lethal amount of rabies virus, allowing the virus-serum mixture to incubate for 1½ hours at a temperture of 37° C. in order to allow the rabies antibody to neutralize the virus, followed by inoculation of the serum-virus mixture into the brains of young mice. Survival of the inoculated mice compared to controls is a measure of the rabies antibody level.

During passage through primary pig kidney tissue the ERA strain of rabies virus occasionally caused some minor cytophatic changes in the tissue cultures. However, the cytopathology was irregular and no correlation was found between cytopathic changes and virus titer. Abelseth Can. Vet. Jour. Vol. 5, No. 4, April 1974, pages 84–87 and especially page 86.

Thus, it is not possible by observation of cytopathic effects to determine the titer of the ERA strain of rabies virus, or measure serum antibody in tissue culture systems.

BRIEF DESCRIPTION OF THE INVENTION

The invention in this case relates to an improved rabies virus strain, to vaccines containing such a strain and to the use of such vaccines in the prevention of rabies in animals.

An object of this invention is to provide a new and improved rabies virus strain.

Another object is to provide a strain of rabies virus which is capable of exhibiting a significantly reproducible cytopathic effect that correlates directly to the titer of the virus.

Still another object of the invention is to provide an improved live attenuated rabies virus vaccine. These and other objects of the invention will be apparent from the description that follows:

GENERAL OUTLINE OF THE INVENTION

The invention relates to a method or preparing a modified attenuated strain of rabies virus capable of producing a significantly reproducible cytopathic effect on a selected cell line and more particularly able to produce a cytopathic effect on the cell line consistent with the virus titer.

The invention further relates to rabies vaccines containing the modified rabies virus strain of the invention.

According to the invention, an improved attenuated strain of rabies virus having a significantly reproducible cytopathic activity is provided. The cytopathic activity of this virus is directly related to its titer, thus providing a unique means for determining when a vaccine of the desired strength has been produced. Vaccines containing the modified virus strain of the invention are highly effective in providing immunity against rabies infection with the production of a minimum of undesired effects when administered to animals.

The improved rabies virus strain of the invention is prepared from the ERA strain of rabies virus. The ERA rabies strain has been identified by Abelseth, M.K., "Propagation of Rabies Virus in Pig Kidney Cell Cultures", Can. Vet. J. 5 84–87 (1964) and Abelseth, M.G., "An Attenuated Rabies Vaccine for Domestic Animals Produced in Tissue Culture", Can. Vet. J. 5 279–286 (1964) as derived from the rabies virus described by Fenje, P., "Propagation of Rabies Virus in Cultures of Hamster Kidney Cells", Can J. Microbiol., 6 379–484 (1960). This ERA strain of rabies virus was deposited with the American Type Culture Collection, Washington, D.C. on Oct. 29, 1964 and recorded there as Number VR 332.

As has been pointed out by Abelseth Can. Vet. Jour. 5 86 the ERA strain, when passed through primary pig kidney cells, occasionally produced cytopathic changes in the cells without any correlation to the virus titer.

According to the instant invention, a new strain of rabies virus, identified herein as the PRI Strain, has been developed by serial passage of the ERA strain through the $PK_2A$ stable pig kidney cell line. This new PRI strain demonstrates a significantly reproducible cytopathic effect that can be used routinely for virus and serum antibody assays.

This is, in addition to its utility in the preparation of vaccines for the immunization of animals against virulent rabies.

The $PK_2A$ pig kidney cell line was initiated from the kidney of an adult pig in November, 1955, by E. Stice of Cutter Laboratories. The cell line was obtained from the Navel Biological Laboratories, San Diego, Calif.

It is found that after about 60 or 70 serial passages, a significantly reproducible cytopathic effect is produced which correlates directly with virus titer. For most consistent results, it has been found that 90 or more serial passages through the $PK_2A$ cell line is desirable.

Generally, passages through the $PK_2A$ cell line is carried out at about 37° C. However, temperatures of about 35° C. -39° C. may be employed.

This novel rabies strain obtained after the desired number of serial passages through the $PK_2A$ cell line is highly immunogenic and is non-pathogenic to animals and may be used in the preparation of rabies vaccine useful for the immunization of such animals as dogs, cats, cattle, horses and swine.

The PRI strain may be serially passed through primary dog kidney cell cultures which are free of adventitious agents in order to provide vaccines having an optimum degree of freedom from such agents. Generally, about 10 or more serial passages are carried out, about 30 to 60 passages being usually employed.

Vaccines containing the PRI rabies virus strain may be diluted with distilled water or any pharmaceutically acceptable injectable fluid such as physiological saline. In addition, a stabilizer such as hydrolyzed gelatin or N-Z-Amine in an amount of about 1 part to 4 parts of virus may be employed in the vaccine.

The novel vaccines of the invention may be administered to animals by intramuscular injection.

Titration of the vaccines of the invention in dogs, cats and other animals shows consistent protection against challenge by such virulent rabies virus strains as CVS-31 and street virus (salivary gland NCDC No. 1545).

In all cases, careful monitoring of the animals failed to disclose any subsequent major reactions or illness due to the vaccine itself.

PREPARATION OF PK$_2$A TISSUE CULTURE

Five to seven day old monolayer culture of the PK$_2$A pig kidney cell line, obtained from the Naval Biological Laboratories, San Diego, Calif., were grown in 32 oz. prescription bottles and subcultured utilizing a trypsin-versine solution. The cells were then planted at the rate of 250,000 cells per 1.0Ml. of LHE (Earles' Balanced Salt Solution plus 0.5% lactalbumin hydrolysate) plus 10% adult or fetal calf serum contained in 16 × 125 mm screw-top tubes. The calf serum had previously been prescreened for rabies antibodies and inhibitors.

REPRODUCTION OF PRI RABIES VIRUS

One day old PK$_2$A tubes were inoculated with 0.2 ml. of virus dilutions. The tubes were allowed to stand at room temperature, protected from light, before being incubated at 37° C., to allow adsorption of the virus to the cell monolayer.

One day after inoculation, the medium in the tubes was replaced by a fresh medium consisting of LHE+8% calf serum and having a pH of 7.4 - 7.6. Subsequently the medium in the tubes was replaced every two days with a fresh medium consisting of LHE+4% calf serum and having a pH of 7.6 - 7.8.

Beginning on the fourth day and ending on the seventh day, the cytopathic effect (CPE) was read. The development of the Rabies CPE was shown first by the sloughing off of different sizes and distribution of rounded cells from the normal cell monolayers. As the infection of the tubes increases, the CPE progresses. Holes and tearing of the cell sheet become more evident with heavily infected tubes showing 70 to 90% distribution over cell sheet if observed long enough.

Serial passages were made in $PK_2A$ cells and tested for infectivity by titration in mice in accordance with techniques described in V-64, and WHO Monograph No. 23, "Laboratory Techniques in Rabies", WHO, Geneva (1966).

The data shown in Table I below, compares the titer of rabies vaccine, based on infectivity in mice ($MLD_{50}$) with the titer of rabies vaccine in $PK_2A$ tissue cultures ($TCID_{50}$) based on cytopathic effects of the PRI virus.

TABLE I

COMPARISON OF TITRATION OF RABIES VIRUS VACCINE IN MICE AND TISSUE CULTURE

| Passage/or Lot | Titer/ml ($log_{10}$) $MLD_{50}$/ml | $TCID_{50}$/ml |
|---|---|---|
| $17PK_2A$ | $10^{5.7}$ | $10^{6.5}$ |
| $43PK_2A$ | $10^{5.2}$ | $10^{5.5}$ |
| $52PK_2A$ | $10^{6.7}$ | $10^{6.8}$ |
| $78PK_2A$ | $10^{7.0}$ | — |
| $82PK_2A$ | $10^{7.5}$ | — |
| $86PK_2A$ | $10^{7.0}$ | — |
| $88PK_2A$ | $10^{7.3}$ | — |
| $88PK_2APEK$ 1 | $10^{7.3}$ | $10^{7.0}$ |
| $148PK_2A$ | $10^{5.7}$ | $10^{6.5}$ |
| $149PK_2A$ | — | $10^{6.2}$ |
| $96PK_2ADK_6$ | $10^{6.1}$ | $10^{7.0}$ |
| $96PK_2ADK_{17}$ | $10^{5.9}$ | $10^{7.0}$ |
| $96PK_2ADK_{23}$ | $10^{5.4}$ | $10^{7.0}$ |
| $96PK_2ADK_{33}$ | — | $10^{6.0}$ |
| $96PK_2ADK_{36}$ | — | $10^{7.0}$ |
| $96PK_2ADK_{40}$ | $10^{5.1}$ | $10^{6.3}$ |
| $96PK_2ADK_{46}$ | $10^{5.3}$ | $10^{6.2}$ |
| $96PK_2ADK_{48}$ | $10^{4.2}$ | $10^{4.3}$ (FD) |
| $96PK_2ADK_{56}$ | $10^{4.9}$ | $10^{6.2}$ |
| $96PK_2ADK_{49}$ | — | $10^{6.5}$ (wet) Lot 12 Ser. 101 |
| $96PK_2ADK_{49}$ | $10^{5.5}$ | $10^{5.9}$ (dry) |
| $96PK_2ADK_{49}$ | — | $10^{6.0}$ (wet) Lot 13 Ser. 102 |
| $96PK_2ADK_{49}$ | $10^{5.0}$ | $10^{5.9}$ (dry) |
| $96PK_2ADK_{49}$ | — | $10^{6.3}$ (wet) Lot 14 Ser. 103 |
| $96PK_2ADK_{49}$ | $10^{5.5}$ | $10^{5.1}$ (dry) |

As shown in Table I, the use of the $PK_2A$ cell system provides a clear method of determining when a sufficient potency has been achieved by observation of the cytopathic effect on the tissue culture cell sheet and without the need for titration in mice.

SERUM NEUTRALIZATION TESTS

Serum dilutions of NCDC Burro serum, with a serum neutralization titer of 1-8000 against 32 $MLD_{50}$ of the CVS strain of rabies virus, were challenged with equal volumes of PRI rabies virus containing approximately 100 -500 $TCID_{50's}$/0.25 ml.

As shown by the data in the following Table II, neutralization of the cytopathic effect by NCDC specific immune rabies antiserum and neutralization of mouse lethality, identify the PRI virus strain as rabies.

TABLE II

NEUTRALIZATION OF PRI RABIES VIRUS VACCINE BY SPECIFIC RABIES ANTISERUM

| Virus | Titer/ml ($Lot_{10}$) | |
|---|---|---|
| $PK_2ADK_{49}$ | $10^{6.5}$ | $TCID_{50}$ |
| $PK_2ADK_{49}$ (Neutralized) | $<10^1$ | $TCID_{50}$ |
| $PK_2ADK_{49}$ | $10^{6.0}$ | $MLD_{50}$ |
| $PK_2ADK_{49}$ | $<10^1$ | $MLD_{50}$ |
| $PK_2ADK_{49}$ - Lot 8, Harvest 9 | | |

Specific Antiserum: NCDC Burro serum with a serum neutralization titer of 1-8000 against 32 $MLD_{50}$ of CVS Virus.

PREPARATION OF VACCINE

Equal aliquots of PRI rabies virus with a titer at approximately $10^4$ $TCID_{50}$/ml. were mixed with stabilizer to give a final concentration of 80% virus and 20% stabilizer. Two cc amber vaccine bottles were then filled to 1.2 cc and freeze-dried.

EFFICACY STUDIES IN DOGS

Susceptible dogs were vaccinated with vaccines prepared from the PRI rabies virus strain and were challenged by intracerebral injection with a fixed rabies virus (CVS). These dogs were challenged by intracerebral injection with a fixed virus (CVS).

The fixed virus was prepared by intracerebral inoculation of CVS-31 into a small puppy. Seven days after inoculation and after the rabies symptoms were observed, the dog was sacrificed. The brain was then removed, ground as a 20% suspension in sterile saline dispensed in 2.0 ml. amounts, and stored at $-60°$ C.

As shown in the followng Table III, titration of the PRI vaccines in dogs indicated that these vaccines afforded consistent protection against this harsh challenge. Further, as the table shows, there was a good correlation of antibody response with protection.

Another group of susceptibel dogs were vaccinated with dilutions of a freeze-dried PRI vaccine (passage $PK_2A96$, $DK_{48}$).

27 days after vaccination, vaccinates and control dogs were challenged with a street virus CNCPC 1545 having a titer of $10^{5.0}$ $MLD_{50}/.03$ ml. by inoculation into both masseter muscles.

As shown by the data in the following Table IV this vaccine provided good protection against this challenge.

TABLE III

SUMMARY - EFFICACY IN DOGS - RABIES VIRUS VACCINE
AGAINST INTRACEREBRAL CHALLENGE
WITH FIXED VIRUS (CVS)

| Passage | No. of Vaccine Dogs | Titer/ml ($\log_{10}$) Dilution | To Vaccine $TCID_{50}$ | $MLD_{50}$ | Antibody Response Pre | Survivors Post | No./Challenged |
|---|---|---|---|---|---|---|---|
| $PK_2A52$ | 6 | $10^0$ | $10^{5.5}$ | $10^{6.7}$ | <4 | 1-420 | 6/6 |
| $PK_2A86$ | 9 | $10^0$ | — | $10^{7.3}$ | <4 | 1-160* | 9/9 |
| $PK_2A88$ | 5 | $10^0$ | $10^{6.3}$ | $10^{7.3}$ | <4 | >1-256 | 5/5 |
| $PK_2A96DK_6$ | 3 | $10^0$ | $10^{6.0}$ | $10^{6.2}$ | <4 | >1-256 | 3/3 |
| $PK_2A96DK_{40}$ | 6 | $10^0$ | $10^{5.3}$ | $10^{5.2}$ | <4 | 1-330 | 6/6 |
|  | 29 |  |  |  |  |  | 29/29 |
| $PK_2A52$ | — | $10^{-1}$ | Not done |  |  |  |  |
| $PK_2A86$ | 6 | " | — | $10^{6.3}$ | <4 | 1-69* | 6/6 |
| $PK_2A88$ | 3 | " | $10^{5.2}$ | $10^{6.3}$ | <4 | 1-107 | 3/3 |
| $PK_2A96DK_6$ | 6 | " | $10^{5.0}$ | $10^{5.2}$ | <4 | 1-130 | 6/6 |
| $PK_2A96DK_{40}$ | 6 | " | $10^{4.3}$ | $10^{4.2}$ | <4 | 1-256 | 6/6 |
|  | 21 |  |  |  |  |  | 21/21 |
| $PK_2A52$ | 6 | $10^{-2}$ | $10^{3.5}$ | $10^{4.7}$ | <4 | 1-192 | 6/6 |
| $PK_2A86$ | 6 | " | — | $10^{5.3}$ | <4 | 1-34* | 6/6 |
| $PK_2A88$ | 4 | " | $10^{4.3}$ | $10^{5.3}$ | <4 | >1-48 | 4/4 |
| $PK_2A96DK_6$ | 6 | " | $10^{4.0}$ | $10^{4.2}$ | <4 | 1-67 | 6/6 |
| $PK_2A96DK_{40}$ | 6 | " | $10^{3.3}$ | $10^{3.2}$ | <4 | 1-150 | 6/6 |
|  | 28 |  |  |  |  |  | 28/28 |
| $PK_2A52$ | 6 | $10^{-3}$ | $10^{2.5}$ | $10^{3.7}$ | <4 | 1-50 | 6/6 |
| $PK_2A86$ | 6 | " | — | $10^{4.3}$ | <4 | <1-32(3)* | 0/3 |
|  |  |  |  |  |  | 1-32(3) | 3/3 |
| $PK_2A88$ | 4 | " | $10^{3.3}$ | $10^{4.3}$ | <4 | <1-32(2) | 0/2 |
|  |  |  |  |  |  | >1-32(2) | 2/2 |
| $PK_2A96DK\ 6$ | 6 | " | $10^{3.0}$ | $10^{3.2}$ | <4 | 1-30 | 2/6 |
| $PK_2A96DK_{40}$ |  | " | $10^{2.3}$ | $10^{2.2}$ | <4 | 1-30 | 3/6 |
|  | 28 |  |  |  |  |  | 19/28 |
| $PK_2A52$ | 4 | $10^{-4}$ | $10^{1.5}$ | $10^{2.7}$ | <4 | <1-20 | 1/4 |
| $PK_2A86$ | 5 | " | — | $10^{3.3}$ | <4 | <1-16* | 5/5 |
| $PK_2A88$ | 3 | " | $10^{2.3}$ | $10^{3.3}$ | <4 | 1-18 | 1/3 |
| $PK_2A96DK_6$ | 3 | " | $10^{2.0}$ | $10^{2.2}$ | <4 | <1-16 | 0/3 |
| $PK_2A96DK_{40}$ |  | Not done |  |  |  |  |  |
|  | 15 |  |  |  |  |  | 7/15 |
| $PK_2A52$ |  | Not done |  |  |  |  |  |
| $PK_2A86$ | 4 | $10^{-5}$ | — | $10^{2.3}$ | <4 | <8 | 0/4 |
| $PK_2A88$ | 4 | " | $10^{1.3}$ | $10^{2.3}$ | <4 | <8 | 0/4 |
| $PK_2A96DK_6$ |  | Not done |  |  |  |  |  |
| $PK_2A96DK_{40}$ |  | Not done |  |  |  |  |  |
|  | 8 |  |  |  |  |  | 0/8 |

(*) Antibody measurement by serum neutralization in mice.

TABLE IV

SUMMARY - EFFICACY IN DOGS - RABIES VIRUS VACCINE
FOLLOWING MASSETER MUSCLE
CHALLENGE - FIXED VIRUS (CVS)

| Passage | No. of Dogs | Dilution | Titer/ml ($\log_{10}$) $TCID_{50}$ | $MLD_{50}$ | Antibody Response Pre | Post | Survivors Total Challenge |
|---|---|---|---|---|---|---|---|
| $PK_2A96\ DK_{46}$ | 4 | $10^0$ | $10^{5.5}$ | $10^{5.3}$ | <4 | >1-256 | 4/4 |
| " | 4 | $10^{-1}$ | $10^{4.5}$ | $10^{4.3}$ | <4 | 1-160 | 4/4 |
| " | 4 | $10^{-2}$ | $10^{3.5}$ | $10^{3.3}$ | <4 | 1-96 | 4/4 |
| " | 4 | $10^{-3}$ | $10^{2.5}$ | $10^{2.3}$ | <4 | 1-56 | 4/4 |
| $PK_2A96DK_{56}$ | 2 | $10^0$ | $10^{5.5}$ | $10^{4.9}$ | <4 | <1-256 | 2/2 |
| " | 4 | $10^{-1}$ | $10^{4.5}$ | $10^{3.9}$ | <4 | 1-160 | 4/4 |
| " | 4 | $10^{-2}$ | $10^{3.5}$ | $10^{2.9}$ | <4 | 1-96 | 4/4 |
| " | 4 | $10^{-3}$ | $10^{2.5}$ | $10^{1.9}$ | <4 | 1-45 | 4/4 |
| Controls (Challenged with $10^{7.2} MLD_{50}$) | 8 | — | — | — | <4 |  | 1/8 |
| $PK_2A88$ | 6 | $10^0$ | ND | $10^{7.0}$ | ND | ND | 6/6 |
| " | 6 | $10^{-1}$ | " | $10^{6.0}$ | " | " | 6/6 |
| " | 6 | $10^{-2}$ | " | $10^{5.0}$ | " | " | 6/6 |
| " | 6 | $10^{-3}$ | " | $10^{4.0}$ | " | " | 6/6 |
| Controls (Challenged with $10^{7.0}MLD_{50}$) | 6 | — | — | — | — | — | 1/6 |

CATTLE

The efficacy of a freeze-dried PRI vaccine was tested in cattle 6 months after vaccination by intramuscular challenge with a street virus, NLDC No. 1545 that had undergone one passage through dog salivary gland.

As shown by the data in the following Table V, the PRI vaccine employed produced protection with a dose of about 100 TCID$_{50}$'s.

CATS

The efficacy of the PRI rabies vaccine in cats is shown by the serologic results given in the following Table VI.

TABLE VI
SEROLOGIC EFFICACY OF PRI RABIES VIRUS VACCINE IN CATS

| Cat# | Virus Dilution | Mouse titer per 0.03 ml | Mouse LD$_{50}$ per 1.0 ml | TC titer per 0.1 ml | TC LD$_{50}$ per 1.0 ml | Pre | Post Vac.* | Post** Chlng. | Conver. |
|---|---|---|---|---|---|---|---|---|---|
| 746 | $10^0$ | 3.91 | 268,500 | 6.0 | 10,000,000 | <4 | 64 | | + |
| 747 | " | | " | | " | " | 64 | | + |
| 752 | " | | " | | " | " | 128 | | + |
| 751 | " | | " | | " | " | >128 | | + |
| 754 | $10^1$ | | 26,850 | | 1,000,000 | <4 | 32 | | + |
| 757 | " | | " | | " | " | 64 | | + |
| 743 | " | | " | | " | " | 32 | | + |
| 741 | " | | " | | " | " | 64 | | + |
| 727 | $10^2$ | | 2,685 | | 100,000 | <4 | 32 | | + |
| 748 | " | | " | | " | " | 16 | | + |
| 725 | " | | " | | " | " | 16 | | + |
| 744 | " | | " | | " | " | 16 | | + |
| 745 | $10^3$ | | 268.0 | | 10,000 | <4 | 8 | | + |
| 739 | " | | " | | " | " | 8 | | + |
| 818 | " | | " | | " | " | 16 | | + |
| 883 | " | | " | | " | " | 4 | | + |
| 884 | $10^4$ | | 26.8 | | 1,000 | <4 | 8 | | + |
| 885 | " | | " | | " | " | 8 | | + |
| 886 | " | | " | | " | " | 16 | | + |
| 887 | " | | " | | " | " | 4 | | + |
| 889 | $10^5$ | | 2.68 | | 100 | <4 | 4 | | + |
| 890 | " | | " | | " | " | 4 | | + |
| 891 | " | | " | | " | " | 8 | | + |
| 892 | " | | " | | " | " | 4 | | + |
| 801 | $10^6$ | | 0.268 | | 10 | <4 | <2 | | − |
| 802 | " | | " | | " | " | <2 | | − |
| 803 | " | | " | | " | " | <2 | | − |
| 804 | " | | " | | " | " | <2 | | − |
| 807 | $10^7$ | | 0.0268 | | 1 | <4 | <2 | | − |
| 808 | " | | " | | " | " | <2 | | − |
| 809 | " | | " | | " | " | <2 | | − |
| 810 | " | | " | | " | " | <2 | | − |
| 812 | Cont. | | | | | <4 | <2 | | − |
| 813 | " | | | | | " | <2 | | − |
| 814 | " | | | | | " | <2 | | − |
| 815 | " | | | | | " | <2 | | − |

Vac. = ERA + 96 psgs. in PK$_2$A + 23 psgs. in DK
* 36 days post vac.
** Chlng. not done

SAFETY

To evaluate the safety of the PRI vaccine, dogs and cats were vaccinated and observed for rabies and other

TABLE V
EFFICACY OF RABIES VIRUS VACCINE IN CATTLE AGAINST STREET VIRUS CHALLENGE*

| Calf No. | Vaccine Dilution | Titer/ml(Log$_{10}$) TCID$_{50}$ | Antibody Pre | Antibody Post* | Survivors No. Challenged** |
|---|---|---|---|---|---|
| 243 | $10^0$ (wet) 2ml | 5.5 | <1-2 | >1-512 | Surv. |
| 244 | " | " | <1-2 | 1-64 | " |
| 245 | " | " | <1-2 | >1-512 | " |
| 246 | $10^0$ (FD) 2ml | 4.8 | <1-2 | >1-128 | Surv. |
| 247 | " | " | <1-2 | >1-128 | " |
| 250 | " | " | ;21 1-2 | >1-128 | " |
| 248 | $10^{-1}$(FD)2ml | 3.8 | <1-2 | ND | Not Chal.*** |
| 251 | " | " | <1-2 | 1-64 | Surv. |
| 252 | " | " | <1-2 | 1-64 | " |
| 253 | $10^{-2}$(FD) 2ml | 2.8 | <1-2 | 1-16 | Surv. |
| 254 | " | " | <1-2 | >1-128 | " |
| 255 | " | " | <1-2 | 1-16 | " |
| 256 | 10thu −3(FD) 2ml | 1.8 | <1-2 | 1-8 | Surv. |
| 257 | " | " | <1-2 | 1-2 | " |
| 258 | " | " | <1-2 | 1-16 | " |
| 259 | $10^{-4}$(FD) 2 ml | 0.8 | <1-2 | 1-8 | Surv. |
| 260 | " | " | <1-2 | 1-2 | Died-Rabies |
| 261 | " | " | <1-2 | <1-2 | Not Chal.*** |
| 219 | Control | — | <1-2 | <1-2 | Died-Rabies |
| 220 | " | — | <1-2 | <1-2 | Surv. |
| 228 | " | — | <1-2 | <1-2 | Died-Rabies |

*Challenged 6 months post vaccination
**Challenged with $10^{6.06}$MLD$_{50}$
***Destroyed - Broken leg, prior to challenge
Vac. = $_{PK2}$A149 untoward effects. Over a period of two years, 914 dogs and more than 100 cats were vaccinated. Careful monitoring failed to reveal any subsequent reactions or illness.

Similarly, tests on swine and other domestic animals showed the PRI rabies virus vaccines of the invention to be safe and effective vaccines for prevention of rabies in animals.

What is claimed is:

1. A method for the preparation of a novel live rabies virus strain which exhibits reproducibly significant cytopathic effect which correlates with the virus titer, said method comprising passing the ERA strain rabies virus in tissue culture of $PK_2A$ cells for a number of passages sufficient to develop said novel strain.

2. The method of claim 1 wherein the passage through the $PK_2A$ cells is repeated at least 60 times.

3. A method for the preparation of a novel live rabies virus exhibiting a reproducibly significant cytopathic effect in $PK_2A$ cells which correlates directly with the virus titer, suitable for immunizing animals against rabies, said method comprising passing the ERA strain rabies virus through tissue cultures of $PK_2A$ cells for at least 60 times and then passing said strain through primary canine kidney cells.

4. A method for the preparation of a novel live rabies virus exhibiting a reproducibly significant cytopathic effect in $Pk_2A$ cells which correlates with the virus titer, said method comprising inoculating cells of the $PK_2A$ cell line with the ERA strain live rabies virus, incubating said virus and cells in a tissue culture nutrient medium for a time sufficient for growth and multiplication of said virus, harvesting said virus and repeating said incubation and harvesting of said virus in at least 60 consecutive cultures of $PK_2A$ cells at intervals of about 4-7 days.

5. A method for the preparation of a novel rabies virus exhibiting a reproducibly significant cytopathic effect in $PK_2A$ cells which correlates with the virus titer and suitable for the immunizing of animals against rabies, said method comprising inoculating cells of a $PK_2A$ cell line with the ERA strain live rabies virus, incubating said virus and cells in a tissue culture medium at a temperature of about 32°-39° C. for a time sufficient for growth and multiplication of said virus, harvesting the virus, repeating said incubation and harvesting of said virus in at least 60 consecutive cultures at intervals of about 4 - 7 days, inculating dog kidney cells with said virus, incubating said virus and cells in a tissue culture medium at a temperature of about 32°-39° C. for a time sufficient for growth and multiplication of said virus to take place, harvesting said virus from said dog kidney cells and repeating said incubation and harvesting of said virus for at least 5 consecutive cultures of said dog kidney cells.

* * * * *